United States Patent [19]

Lugosi et al.

[11] 4,435,567

[45] Mar. 6, 1984

[54] PROCESS FOR PREPARING SUBSTITUTED UREA DERIVATIVES

[75] Inventors: György Lugosi, Göd-felso; Antal Simay, Budapest; Janos Bodnar, Budapest; Laszlo Simandi, Budapest; Eva Somfai, Budapest, all of Hungary

[73] Assignee: Chinoin Gyogyszer es Vesgyeszeti Termekek Gyara R. T., Budapest, Hungary

[21] Appl. No.: 334,470

[22] Filed: Dec. 28, 1981

[30] Foreign Application Priority Data

Dec. 29, 1980 [HU] Hungary ................ 3135/80

[51] Int. Cl.$^3$ ............... C07C 127/00; C07C 127/15; C07C 127/17; C07C 127/19
[52] U.S. Cl. .................. 544/165; 546/143; 546/146; 548/127; 548/128; 548/135; 548/140; 548/163; 548/167; 548/337; 548/341; 560/34; 564/47; 564/48; 564/50; 564/52; 564/53; 564/54; 564/55; 564/56; 564/57; 564/59; 564/60; 564/61
[58] Field of Search ............ 564/48, 50, 52, 53, 564/54, 55, 57, 59, 60, 61, 47, 56; 560/34; 544/165; 546/143, 146; 548/127, 128, 135, 140, 163, 167, 337, 341

[56] References Cited

FOREIGN PATENT DOCUMENTS 2091257 7/1982 United Kingdom ............ 564/48

OTHER PUBLICATIONS

Theilheimer, *Synthetic Methods of Organic Chemistry*, vol. 16, #434, Basel–Karger Publishers, N.Y., N.Y.
Shioyama et al., CA78: 124577y (1973).
McClelland et al., CA 42: 907h (1947).
Klyuev et al., CA 71: 22053n (1969).

*Primary Examiner*—Thomas A. Waltz
*Attorney, Agent, or Firm*—Karl F. Ross; Herbert Dubno

[57] ABSTRACT

A process for the preparation of substituted urea derivatives, and compositions and concentrates for the same purpose are disclosed. According to the process the substituted urea derivatives of formula (I)

$$R-NH-\underset{\underset{O}{\|}}{C}-N\underset{R^2}{\overset{R^1}{\diagup}}$$

wherein
R is hydrogen, alkyl, aryl, cycloalkyl or aralkyl, $R^1$ and $R^2$ are hydrogen, alkyl, alkenyl, alkinyl, alkoxy, oxyalkyl, cycloalkyl, aralkyl, alkoxycarbonylalkyl, aryl or heteroaryl, or $R^1$ and $R^2$ together with the adjacent nitrogen atom may form a saturated or unsaturated heterocycle, or a condensed and/or substituted ring system, and said heterocycle or said condensed and/or substituted ring system may contain also a sulfo group, can be manufactured by reacting an amine of formula (II)

$$R^1\diagdown NH \atop R^2\diagup$$

with an N-carbamoyl-benzoic acid sulfimide derivative of formula (III)

$$R-NH-\underset{\underset{O}{\|}}{C}-N\diagdown \underset{\underset{\|}{C}}{\overset{S\diagup\diagdown O}{}}\diagup$$

The disclosed N-acylating composition comprises of from 3 to 60% by weight, preferably of from 5 to 50% by weight sulfimide derivative of formula (III), of from 97 to 40% by weight, preferably of from 95 to 50% by weight solvent, and if desired, an organic or inorganic base.

The disclosed N-acylating concentrate comprises of from 60 to 95.5% by weight N-acylating agent of formula (III) and of from 4.5 to 40% by weight additives.

1 Claim, No Drawings

PROCESS FOR PREPARING SUBSTITUTED UREA DERIVATIVES

Among the substituted urea derivatives there are compounds showing significant biological activity, and many of them are used as medicaments in treating human beings, animals or plants. So for example $N^1$-p-aminobenzenesulfonyl-$N^2$-n-butylurea, $N^1$-p-methylbenzenesulfonyl-$N^2$-n-butylurea and $N^1$-4-[2-(2-methoxy-5-chlorobenzamido)-ethyl]-benzenesulfonyl-$N^2$-cyclohexylurea are active ingredients of medical preparations against diabetes, methyl-1-butylcarbamoyl-benzimidazole-2-yl-carbamate shows fungicidal effect, 3-(4-bromo-3-chlorophenyl)-1-methoxy-1-methylurea has herbicidal effect, and 1-(4-chlorophenyl)-3-(2,6-difluorobenzoyl)-urea shows insecticidal activity.

The present invention relates to a composition and a preparation process for preparing substituted urea derivatives of formula (I)

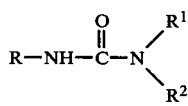

wherein
R is hydrogen, alkyl, aryl, cycloalkyl or aralkyl,
$R^1$ and $R^2$ are hydrogen, alkyl, alkenyl, alkinyl, alkoxy, oxyalkyl, cycloalkyl, aralkyl, alkoxycarbonylalkyl, aryl or heteroaryl, or $R^1$ and $R^2$ together with the adjacent nitrogen atom may form a saturated or unsaturated heterocycle, or a condensed and/or substituted ring system, and said heterocycle or said condensed and/or substituted ring system may contain also a sulfo group.

The meanings of R, $R^1$ and $R^2$ are as defined above throughout the description.

In our specification the term "alkyl group" means a straight-chain or branched alkyl group which optionally may be further substituted; it may be substituted for example by halogen, alkoxy, hydroxy or amino.

The aryl group is preferably a phenyl or naphthyl group, any of which may be further substituted by one or more substituents, for example halogen, alkyl, alkoxy, nitro, amino or trifluoromethyl.

The aralkyl group is preferably a benzyl or phenethyl group.

The term "heteroaryl group" is used to designate a group containing one or more hetero atoms, for example the benzthiazolyl or the thiadiazolyl group.

$R^1$ and $R^2$ together with the adjacent nitrogen atom may form a heterocycle, for example morpholino, isoquinolyl, tetrahydroisoquinolyl, benzimidazolyl; any of these groups may be further substituted.

The most generally used preparation process for manufacturing substituted urea derivatives was based on the addition reaction of the amines of formula (II)

to isocyanates. A disadvantage of this process is that isocyanates are in general very irritative to the mucous membranes and are extremely toxic, so their storage, transport and application in the technological process cause very serious labor safety problems. A further disadvantage is that said addition reaction is a strongly exothermic one; which, in particular when isocyanates having low boiling point are used, may cause technological problems and undesired side effects.

Another known process for preparing substituted urea derivatives is reacting amines with monosubstituted carbamic acid chlorides. However, carbamic acid chlorides are unstable compounds which decompose by formation of hydrochloric acid, so their storage is difficult.

A further known method for manufacturing substituted urea derivatives reacts amines with phosgene, then acylating the corresponding amines with the obtained carbamoylchloride derivatives. The disadvantage of this process lies in the necessity of using the toxic phosgene.

It has surprisingly been found that urea derivatives of formula (I) having a high purity can be produced with a good yield and by a reaction easy to carry out, if the amines of formula (II) are reacted with the N-carbamoyl-benzoic acid sulfimides of formula (III)

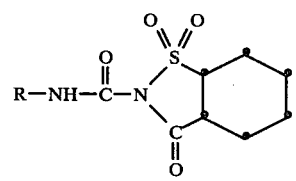

The reaction is performed in an organic solvent, in water or in the mixture of water and of an organic solvent in the presence of a base. As an organic solvent there may be used e.g. a hydrocarbon, a ketone (e.g. aceton or methylethylketone), an ester (e.g. ethylacetate), an ether (e.g. dioxane or tetrahydrofurane), a chlorinated solvent (e.g. chloroform or dichloromethane), a lower acid amide (e.g. formamide or dimethylformamide).

The solvent is to be chosen using knowledge of solubility values of the starting materials and those of the endproducts. The solvent used should make it possible to isolate the urea derivative of formula (I) in a pure form, either in an insoluble form precipitated from the mixture, or by diluting the mixture with another solvent and thereby precipitating the product. Meanwhile the starting materials and the by-products should remain dissolved.

As a base there may be used a tertiary amine, preferably triethylamine, or an inorganic base, preferably an alkali metal hydroxide, alkali metal carbonate or an alkali metal bicarbonate; the excess of the amine of formula (II) may also be applied. Using organic bases is more advantageous, because they form salt-like adducts with benzoic acid sulfimide, and these adducts show a good solubility in some systems in which the obtained urea derivatives are insoluble.

The amines and the N-carbamoyl-benzoic acid sulfimides react easily at a temperature of from 0° C. to 100° C., preferably at ambient temperature.

The obtained urea derivatives are isolated by crystallization or by precipitation with a suitable solvent. In the meantime the benzoic acid sulfimide split off in the reaction forms a salt with the applied base and this salt remains dissolved.

The sulfimide can easily be recovered, if desired, and it may be used for the preparation of the N-carbamoyl-benzoic acid sulfimide to be applied in the next cycle of the process.

The main advantage of our new process is that it avoids use of the strongly toxic liquid or gaseous acylating agents. The N-carbamoyl-benzoic acid sulfimides applied in our process as acylating agents are solid, crystalline, slightly toxic materials, which are simple to store, to transfer and to handle. A further advantage of their application is that the acylation reaction carried out by their aid is less exothermic than for example the reaction with isocyanates, and thereby harmful side reactions can be avoided and the end-products can be produced in a very pure form and generally with a good yield.

A further aspect of the invention is a composition suitable for N-acylation of organic molecules. This composition consists of an acylating agent, which is an N-carbamoyl-benzoic acid sulfimide derivative, a solvent, and an organic or inorganic base, if desired. As a solvent there can be used an organic solvent, a mixture of an organic solvent and of water, or water alone.

The acylating composition of our invention may be used for N-acylation of organic amines by chemically reacting the amines of formula (II) with the acylating composition; the urea derivatives of formula (I) are obtained.

The acylating composition according to our invention is prepared by admixing a compound of formula (III) with a solvent, and, if desired, with an organic or inorganic base.

The acylating composition of our invention contains 3 to 60% acylating agent, preferably from 5 to 50% acylating agent, the amount depending upon the kind of the solvent used in the composition.

The amount of the solvent used in the composition is of from 97 to 40%, preferably of from 95 to 50%; as solvents, ketones and/or esters and/or ethers and/or chlorinated solvents are used. Lower acid amides can also be applied. The composition may contain also from 0.01 to 30% organic or inorganic base, if desired.

According to our invention the novel composition can be used for N-acylating organic, N-containing molecules as described above.

A great number of amines can be N-acylated with a good yield with a composition consisting of from 8 to 35% by weight acylating agent, of from 92 to 55% by weight acetone or aqueous acetone and, if desired, of from 0.5 to 15% by weight triethylamine.

The composition can be stored in a ready state and it can be transferred to the place of application when it is desired.

The invention relates also to concentrates, which after dilution are suitable for N-acylation of organic molecules.

The above mentioned concentrates consist of from 60 to 95.5% by weight acylating agent of formula (III) and additives.

As additives there can be used organic bases in an amount of from 4.5 to 40% by weight, or solvents in the same amounts. In case the acylating agent of formula (III) is intended to be used for N-acylation of less sensitive molecules, the additive may be a by-product of the preparation reaction which does not disturb the acylation reaction.

The concentrates of the invention are easy to store, to pack and to transfer, which do not apply to the isocyanates former used for N-acylation. For storing and transferring the isocyanates one needed special tanks, in particular in the case of methylisocyanate.

The concentrate must be diluted with a solvent before use. The solvents enumerated above are very suitable for this purpose.

The following non-limiting examples illustrate the invention.

EXAMPLE 1

A mixture of 1.0 g cyclohexylamine and 5 ml aceton was added dropwise to a suspension of 1.5 g phenylcarbamoyl-benzoic acid sulfimide with 20 ml aceton, under stirring. The reaction mixture was stirred for 80 minutes at room temperature, then diluted with 150 ml water. The precipitated solid product was cooled, filtered, washed with water and dried. 1.0 g 1-phenyl-3-cyclohexylurea was obtained with a melting point of from 182° to 184° C.

EXAMPLE 2

A mixture of 1.1 g benzylamine and 5 ml aceton was added dropwise to a suspension of 1.5 g phenylcarbamoyl-benzoic acid sulfimide with 20 ml aceton, under stirring. The reaction mixture was stirred for 35 minutes at room temperature, then diluted with 150 ml water and cooled to 5° C. The precipitated solid product was filtered, washed with water and dried. 1.02 g 1-phenyl-3-benzylurea was obtained with a melting point of from 170° to 172° C.

EXAMPLE 3

A solution of 0.9 g morpholine with 5 ml aceton was added dropwise during 5 minutes to a suspension of 1.5 g phenylcarbamoyl-benzoic acid sulfimide with 20 ml acetone, under stirring. The reaction mixture was stirred for a further 30 minutes at ambient temperature, then diluted with 150 ml water. Acetone was distilled off, the mixture was cooled, and 0.35 g phenylcarbamoyl-morpholine was isolated by filtration. The white crystalline material melted at 160°–162° C.

EXAMPLE 4

A solution of 1.35 g 1,2,3,4-tetrahydroisoquinoline with 5 ml aceton was added dropwise to a suspension of 1.5 g phenylcarbamoyl-benzoic acid sulfimide with 20 ml aceton, at ambient temperature. The reaction mixture was stirred for 45 minutes, then diluted with 150 ml water, cooled to 5° C. and the precipitated crystalline product was filtered, washed with water and dried. 1.18 g N-phenylcarbamoyl-1,2,3,4-tetrahydroisoquinoline was obtained with a melting point of 145°–146° C.

EXAMPLE 5

A solution of 0.75 g i-propylamine with 5 ml aceton was added dropwise to a suspension of 1,5 g phenylcarbamoyl-benzoic acid sulfimide with 10 ml acetone, under stirring. The reaction mixture was stirred for 30 minutes at ambient temperature, then diluted with 50 ml water and cooled. The 0.75 g crystalline 1-phenyl-3-i-propylurea was isolated by filtration (melting point: 158°–160° C.).

EXAMPLE 6

0.70 g glycineesterhydrochloride was added to a suspension of 1.5 g phenylcarbamoyl-benzoic acid sulfimide with 15 ml dimethylformamide. To the obtained mixture there was added 1.4 ml triethylamine dropwise, at ambient temperature under stirring. The reaction mixture was stirred for 60 minutes, then diluted with 150 ml water, and cooled during a night. 0.50 g 1-phenyl-3-ethoxycarbonylmethylurea was obtained as a crystalline product melting at 113°–114° C.

EXAMPLE 7

A solution of 0.65 g ethanolamine with 5 ml aceton was added dropwise to a suspension of 1.5 g phenylcarbamoyl-benzoic acid sulfimide with 10 ml aceton, under stirring. The reaction mixture was stirred for a further 30 minutes at ambient temperature, evaporated in vacuo, the residue was triturated with 20 ml water, and the obtained solid product was filtered, dried and recrystallized. There was obtained 0.25 g 1-phenyl-3-(2-hydroxyethyl)-urea, melting at 120°–122° C.

EXAMPLE 8

1 ml of an aqueous ammonium hydroxide solution (25%) was added dropwise to a suspension of 1.5 g phenylcarbamoyl-benzoic acid sulfimide with 20 ml acetone, under stirring. The reaction mixture was stirred for 30 minutes at ambient temperature, then evaporated in vacuo and the residue was crystallized from water. 0.60 g phenylurea melting at 148°–150° C. was obtained.

EXAMPLE 9

A mixture of 0.40 g ethylenediamine and 5 ml aceton was added dropwise to a suspension of 1.5 g phenylcarbamoyl-benzoic acid sulfimide with 15 ml acetone, under stirring. The reaction mixture was stirred for 45 minutes, diluted with 50 ml water, cooled, the precipitated solid product was filtered, washed with water and dried. 0.62 g N,N'-bis(phenylcarbamoyl)-ethylenediamine was obtained, melting above 240° C.

EXAMPLE 10

A solution of 0.8 g 3-amino-benzotrifluoride and 0.7 ml triethylamine with 5 ml aceton was added dropwise to a suspension of 1.2 g methylcarbamoyl-benzoic acid sulfimide with 15 ml aceton, under stirring. The reaction mixture was stirred at ambient temperature for 4 hours, then evaporated in vacuo, and the residue was recrystallized from aqueous alcohol. 1-methyl-3-(3-trifluoromethyl)-phenylurea, melting at 114°–116° C., was obtained.

EXAMPLE 11

A solution of 0.6 g o-methoxyaniline and 0.7 ml triethylamine with 5 ml aceton was added dropwise to a suspension of 1.5 g phenylcarbamoyl-benzoic acid sulfimide, under stirring. The reaction mixture was stirred at room temperature for 2 hours, then diluted with 100 ml water. The precipitated solid product was cooled, filtered, washed with water and dried. 0.80 g 1-phenyl-3-(4-methoxyphenyl)-urea was obtained, which melted at 196°–198° C.

Analysis results ($C_{14}H_{14}N_2O_2$): Calculated: C=69.40%; H=5.82%; N=11.57%; Found: C=69.21%; H=5.54%; N=11.38%.

EXAMPLE 12

A solution of 0.5 g aminopyridin and 0.7 ml triethylamine with 5 ml acetone was added dropwise to a suspension of 1.5 g phenylcarbamoyl-benzoic acid sulfimide with 15 ml aceton, under stirring. The reaction mixture was stirred for 45 minutes at room temperature, then diluted with 100 ml water. The acetone was distilled off, the residue was cooled, and the precipitated solid product was filtered, washed with water and dried. 0.6 g 1-phenyl-3-(2-pyridyl)-urea was obtained with a melting point of 185°–186° C.

EXAMPLE 13

1.55 g n-butylcarbamoyl-benzoic acid sulfimide was suspended in 5 ml aceton, and to the suspension there were added 0.80 ml triethylamine and 0.95 g benzimidazole-(2)-carbamic acid methylester. The reaction mixture was stirred at room temperature for 3 hours, then cooled to 5° C., the solid product was evacuated, washed with a 1:1 mixture of water and acetone, and dried. 1.40 g 1-butylcarbamoyl-benzimidazole-(2)-carbamic acid methylester was obtained, melting at 331°–336° C. (recrystallizes between 220° C. and 230° C.).

EXAMPLE 14

6.32 g benzylcarbamoyl-benzoic acid sulfimide was suspended in 40 ml of a 1:1 mixture of water and aceton. 2.55 g p-chloroaniline was added to the suspension, then a solution of 2.8 ml triethylamine with 10 ml of a 1:1 water-aceton mixture was added dropwise at ambient temperature during a half hour. The reaction mixture was stirred for 5 hours at room temperature, the obtained product was evacuated, washed with a 1:1 mixture of water and aceton and dried. 4.3 g 1-(4-chlorophenyl)-3-benzylurea was obtained, which melted at 206°–208° C.

EXAMPLE 15

6.16 g cyclohexylcarbamoyl-benzoic acid sulfimide was suspended in 20 ml of a 1:1 mixture of water and acetone. To the suspension a solution of 3.45 g p-chloro-o-nitraniline and 2.8 ml triethylamine with 10 ml acetone was added dropwise, then the process of example 1 was followed. 4.75 g 1-(4-chloro-2-nitrophenyl)-3-cyclohexylurea was obtained with a melting point of 115°–116° C.

Analysis results ($C_{13}H_{16}ClN_3O_3$): Calculated: C=52.44%; H=5.42%; N=14.11%; Cl=11.91%; Found: C=52.20%; H=5.30%; N=14.10%; Cl=11.73%.

EXAMPLE 16

5.08 g ethylcarbamoyl-benzoic acid sulfimide was reacted with 1.86 g aniline and 2.8 ml triethylamine in 20 ml of a 1:1 mixture of water and acetone, as described in example 1. 2.59 g 1-phenyl-3-ethylurea was obtained, melting at 99°–100° C.

EXAMPLE 17

5.64 g n-butylcarbamoyl-benzoic acid sulfimide was reacted with 2.14 g p-toluidine and 2.8 ml triethylamine in 20 ml of a 1:1 mixture of water and acetone, as described in example 1. 3.28 g 1-(p-tolyl)-3-(n-butyl)-urea was obtained, melting at 118°–119° C.

EXAMPLE 18

11.28 g n-butylcarbamoyl-benzoic acid sulfimide was reacted with 2.16 g o-phenylene diamine and 5.6 ml triethylamine in 20 ml of a 1:1 mixture of water and acetone, as described in example 1. 5.0 g N,N'-bis(n-butylcarbamoyl)-o-phenylene diamine was obtained, melting at 163°–164° C.

Analysis results ($C_{16}H_{26}N_4O_2$): Calculated: C=62.74%; H=8.52%; N=18.29%; Found: C=62.20%; H=8.70%; N=18.15%.

EXAMPLE 19

50 g N-(3-trifluoromethyl)-phenylcarbamoyl-benzoic acid sulfimide was suspended in 250 ml aceton, then a mixture of 25 ml of a 60% aqueous dimethylamine solution and of 25 ml acetone was added thereto dropwise, during 40 minutes, under stirring and ice-water cooling. The reaction mixture was stirred for a further hour at room temperature, the acetone was distilled off, the residue was heated in 200 ml distilled water to 60° C., and was stirred for an hour. The suspension was cooled with icy water to 5° C., crystallized for a half hour, and the precipitated crystals were filtered, washed twice with 50—50 ml of cooled distilled water, then dried till constant weight was reached. 30.6 g N-(3-trifluoromethyl)-phenyl-N'-dimethylurea was obtained, melting at 152°–153° C.

EXAMPLE 20

10 g N-(3,4-dichloro)-phenylcarbamoyl sulfimide was suspended in 50 ml acetone, then a mixture of 4,2 ml 60% aqueous dimethylamine and 4.2 ml acetone was added thereto dropwise, in 40 minutes under stirring and ice-water cooling. After the addition the reaction mixture was stirred for a further hour at room temperature, then evaporated. The residue was stirred in 100 ml distilled water at 60° C. for an hour, then cooled to 5° C. by ice-water cooling. After a further half hour stirring the precipitated crystals were filtered, washed twice with 10—10 ml cooled distilled water and dried till constant weight was reached. 5.4 g N-(3,4-dichloro)-phenyl-N',N'-dimethylurea was obtained, melting at 155°–157° C.

EXAMPLE 21

10 g N-(4-chloro)-phenylcarbamoyl sulfimide was suspended in 50 ml aceton and 2.43 g N-methyl-N-(1-methyl-prop-2-inyl)-amine was added to the reaction mixture under ice-water cooling, then a mixture of 4.2 ml triethylamine and 4.2 ml acetone was added dropwise under stirring, during 40 minutes. The mixture was stirred at room temperature for an hour, then solvent was completely removed by evaporation. The residue was suspended in 100 ml distilled water, stirred at 60° C. for an hour, then cooled with ice-water to 5° C. After a half hour stirring the precipitated crystals were filtered, washed twice with 10—10 ml cooled distilled water and dried. 6,1 g N-(4-chloro)-phenyl-N'-methyl-N'-(1-methyl-prop-2-inyl)-urea was obtained, melting at 134°–136° C.

EXAMPLE 22

10 g N-methylcarbamoyl-benzoic acid sulfimide was suspended in 30 ml aceton, and to the suspension there was added 6.25 g 2-benzthiazol-amine under ice-water cooling, then a mixture of 5.8 ml triethylamine and 5.8 ml acetone was added thereto dropwise, under cooling and stirring, during 40 minutes. The cooling was stopped, and the reaction mixture was stirred for a further hour at room temperature, then the N-2-benzthiazolyl-N'-methylurea was crystallized by addition of 80 ml water. The suspension was cooled to 5° C., after a half hour stirring the precipitated crystals were filtered, washed twice with 10—10 ml portions of cooled distilled water and dried. 7.0 g product was obtained, sublimating at 287° C.

EXAMPLES 23 TO 30

The process described in example 5 was followed using the starting materials given in table 1. The amount of the N-carbamoyl-benzoic acid sulfimide was 10 g in each example. "CBS" is used for "carbamoyl-benzoic acid sulfimide".

TABLE 1

| Example | N—carbamoyl-benzoic acid sulfimide | Amount of triethylamine | Kind and amount of the reagent | Name and amount of the end-product | Melting point |
|---|---|---|---|---|---|
| 24 | N—(3,4-dichloro)-phenyl-CBS | 3.8 ml | N—methoxy-N—methyl-amine; 1.32 g | N'—(3,4-dichloro)-phenyl-N—methyl-N—methoxyurea; 5.44 g | 90–92° C. |
| 23 | N—phenyl-CBS | 4.6 ml | dimethylamine (gas) in acetone; 1.5 g | N—phenyl—N',N'—dimethylurea; 4.78 g | 130–132° C. |
| 25 | N—methyl-CBS | 5.8 ml | N—2-benzthiazolyl-N—methylamine; 6.83 g | N—2-benzthiazolyl-N,N'—dimethylurea; 7.84 g | 118–119° C. |
| 26 | N—(4-chloro)-phenyl-CBS | 4.2 ml | dimethylamine (gas) in acetone; 1.34 g | N'—(4-chloro)-phenyl-N,N—dimethylurea; 5.49 g | 169–172° C. |
| 27 | N—(3,4-dichloro)-phenyl-CBS | 3.8 ml | N—methyl-N—butylamine; 2.34 g | N'—(3,4-dichloro)-phenyl-N—methyl-N—butylurea; 6.45 g | 101–102° C. |
| 28 | N—phenyl-CBS | 4.6 ml | 1-(2-methyl)-cyclohexylamine; 3.74 g | N—(2-methyl)-cyclohexyl-N'—phenylurea; 6.61 g | 133–135° C. |
| 29 | N—methyl-CBS | 5.8 ml | N—(5-[1,1-dimethylethyl]-1,3,4-thiadiazol-2-yl)-N—methylamine; 7.13 g | N—(5-[1,1-dimethylethyl]-1,3,4-thiadiazol-2-yl)-N,N'—dimethylurea; 7.61 g | 158–160° C. |
| 30 | N—methyl-CBS | 5.8 ml | N—(5-/trifluoromethyl-1,3,4-thiadiazol-2-yl)-N—methylamine; 7.63 g | N—(5-[trifluoromethyl]-1,3,4-thiadiazol-2-yl)-N,N'—dimethylurea; 8.21 g | 133–134° C. |

We claim:

1. A process for the preparation of a urea derivative of formula (I)

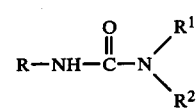

wherein

R is hydrogen, alkyl, aryl, cycloalkyl or aralkyl, $R^1$ and $R^2$ are hydrogen, alkyl, alkenyl, alkinyl, alkoxy, oxyalkyl, cycloalkyl, aralkyl, alkoxycarbonylalkyl, aryl or heteroaryl, or $R^1$ and $R^2$ together with the adjacent nitrogen atom may form a saturated or unsaturated heterocycle, or a condensed and/or substituted ring system, and said heterocycle or said condensed and/or substituted ring system may contain also a sulfo group,
which comprises reacting an amine of formula (II)

with an N-carbamoyl-benzoic acid sulfimide in a composition consisting essentially of 3 to 60% by weight of a sulfimide of formula (III)

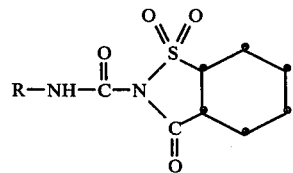

wherein R is hydrogen, alkyl, aryl, cycloalkyl or aralkyl, as an N-acylating agent and of from 97 to 40% by weight, preferably of from 95 to 50% by weight solvent as an additive, and 0.01 to 30% by weight organic or inorganic base.